United States Patent
Lee et al.

(10) Patent No.: US 10,980,991 B2
(45) Date of Patent: Apr. 20, 2021

(54) FLEXIBLE MICRONEEDLE FOR DENTAL MATERIAL DELIVERY AND METHOD OF MANUFACTURING THE SAME

(71) Applicant: B&L BIOTECH, INC., Gyeonggi-do (KR)

(72) Inventors: In Whan Lee, Seoul (KR); Gil Hwan Sung, Seoul (KR); Seung Ki Baek, Seoul (KR); In Jeong Choi, Seoul (KR)

(73) Assignee: B&L BIOTECH, INC., Ansan-si (KR)

( * ) Notice: Subject to any disclaimer, the term of this patent is extended or adjusted under 35 U.S.C. 154(b) by 561 days.

(21) Appl. No.: 15/248,610

(22) Filed: Aug. 26, 2016

(65) Prior Publication Data

US 2017/0080196 A1    Mar. 23, 2017

(30) Foreign Application Priority Data

Sep. 21, 2015 (KR) .................. 10-2015-0133325

(51) Int. Cl.
*A61M 37/00* (2006.01)
*A61C 19/06* (2006.01)
(Continued)

(52) U.S. Cl.
CPC ....... *A61M 37/0015* (2013.01); *A61C 19/063* (2013.01); *A61L 31/041* (2013.01);
(Continued)

(58) Field of Classification Search
CPC ...... A61M 37/0015; A61M 2037/0023; A61M 2037/0046; A61M 2037/0053;
(Continued)

(56) References Cited

U.S. PATENT DOCUMENTS

| 2004/0106904 A1* | 6/2004 | Gonnelli | A61B 17/205 604/173 |
| 2008/0125743 A1* | 5/2008 | Yuzhakov | A61M 37/0015 604/506 |

(Continued)

FOREIGN PATENT DOCUMENTS

| CN | 104706626 A | 6/2015 |
| JP | 2010-29634 A | 2/2010 |

(Continued)

OTHER PUBLICATIONS

Wang et al., Colloids and Surfaces B; Biointerfaces, Elsevier, Jan. 10, 2015, pp. 520-530, vol. 126.

(Continued)

*Primary Examiner* — Robert A Wax
*Assistant Examiner* — Quanglong N Truong
(74) *Attorney, Agent, or Firm* — Sughrue Mion, PLLC

(57) ABSTRACT

Disclosed is a microneedle for dental material delivery, the microneedle including a needle body portion; an active ingredient coating portion configured to coat the surface of the needle body portion, and including an active ingredient transferred to the skin tissue within a mouth; and a base portion configured to couple with the needle body portion, and to bend along a skin shape within the mouth, wherein the base portion includes at least one of polyethylene (PE), polypropylene (PP), polytetrafluoroethylene (PTFE), polymethylmethacrylate (PMMA), ethylene vinyl acetate (EVA), polycaprolactone (PCL), polyurethane (PU), polyethylene terephthalate (PET), polyethylene glycol (PEG), polyvinyl alcohol (PVA), poly lactide (PLA), poly lactic-co-glycolic acid (PLGA), and polyglycolide (PGA).

15 Claims, 11 Drawing Sheets

(51) Int. Cl.
  *A61L 31/04* (2006.01)
  *A61L 31/08* (2006.01)
  *A61L 31/10* (2006.01)
  *A61L 31/16* (2006.01)
(52) U.S. Cl.
  CPC ............... *A61L 31/08* (2013.01); *A61L 31/10* (2013.01); *A61L 31/16* (2013.01); *A61L 2300/402* (2013.01); *A61L 2300/606* (2013.01); *A61L 2420/02* (2013.01); *A61L 2430/12* (2013.01); *A61M 2037/0023* (2013.01); *A61M 2037/0046* (2013.01); *A61M 2037/0053* (2013.01); *A61M 2037/0061* (2013.01)
(58) Field of Classification Search
  CPC ........ A61L 31/08; A61L 31/041; A61L 31/10; A61L 31/16; A61L 2430/12; A61L 2420/02; A61L 2300/606; A61L 2300/402; A61C 19/063
  See application file for complete search history.

(56) References Cited

U.S. PATENT DOCUMENTS

| | | | |
|---|---|---|---|
| 2008/0213461 A1* | 9/2008 | Gill | A61K 9/0021 427/2.3 |
| 2012/0136312 A1* | 5/2012 | Terahara | A61B 5/150984 604/173 |
| 2012/0330250 A1 | 12/2012 | Kuwahara et al. | |
| 2013/0273135 A1* | 10/2013 | Brooks | A61L 27/34 424/426 |
| 2014/0066842 A1 | 3/2014 | Zhang et al. | |
| 2014/0276378 A1* | 9/2014 | Chen | A61M 37/0015 604/46 |

FOREIGN PATENT DOCUMENTS

| | | |
|---|---|---|
| JP | 2010-131123 A | 6/2010 |
| JP | 2014-532482 A | 12/2014 |
| JP | 2015-515474 A | 5/2015 |
| JP | 2015-109963 A | 6/2015 |
| KR | 10-2014-0141360 A | 12/2014 |
| KR | 10-1549086 B1 | 9/2015 |
| WO | 2013-063614 A1 | 5/2013 |
| WO | 2013-152092 A1 | 10/2013 |

OTHER PUBLICATIONS

Communication dated May 2, 2017 from the Japanese Patent Office in counterpart application No. 2016-174409.

Communication dated Mar. 22, 2019, issued by the German Patent Office in counterpart German Patent Application No. 102016115910.7.

* cited by examiner

FLEXIBLE MICRONEEDLE FOR DENTAL MATERIAL DELIVERY AND METHOD OF MANUFACTURING THE SAME

CROSS-REFERENCE TO RELATED APPLICATION

This application claims the priority benefit of Korean Patent Application No. 10-2015-0133325, filed on Sep. 21, 2015, in the Korean Intellectual Property Office, the disclosure of which is incorporated herein by reference.

BACKGROUND

1. Field of the Invention

Example embodiments relate to a microneedle for dental material delivery and a method of manufacturing the microneedle, and more particularly, a microneedle for dental material delivery that may be attached to the gums having a curved surface and may deliver a dental material to an inside of the gums and a method of manufacturing the microneedle.

2. Related Art

In the dental treatment according to the related art, a transdermal drug composition method has generally employed a method of penetrating the skin within a mouth using a syringe. This method may cause pain and significant stress on a patient side.

In the recent times, research on a microneedle has been actively conducted as a new transdermal delivery method to outperform the above issue. In general, if the microneedle is a device for supplying the nutrition or facilitating the penetration of a medical substance by stimulating the skin or making a small hole on the skin using a small size of a needle, a type of the microneedle is not particularly limited. In general, the microneedle has a diameter of about 1 µm to about 100 µm.

When using the microneedle configured as above, the medical substance may be locally delivered to the cell or tissue without causing significant pain. Further, the microneedle may be effectively used to administer molecules, such as peptide, protein, oligonucleotide, DNA, etc., incapable of infiltrating into the biological membrane or to target-deliver the medical substance to a part hard to be treated and a specific portion or tissue of a body.

The microneedle may have four types, for example, a solid microneedle, a coating microneedle, a melting-type microneedle, a hollow microneedle.

Here, the melting-type microneedle employs a method in which, once the melting-type microneedle is applied to the skin, a microneedle material starts being melted and a medical substance contained therein is delivered to the skin. Using this microneedle, the medical substance may be delivered with a one-time administration and the microneedle does not remain and thus, the risk of pollution is absent.

Here, a relatively long period of time, for example, 10 minutes or more, is required to melt the melting-type microneedle due to the moisture in the skin after administration. Since an active ingredient contained in the microneedle is subject to the complete melting of the microneedle, a fixed amount of medical substance may not be readily delivered to the skin. In addition, the melting-type microneedle is to be manufactured based on molding. Thus, a relatively long manufacturing time is required and the active ingredient may vary due to a manufacturing temperature.

Meanwhile, the coating microneedle may be simply manufactured and may quickly deliver a medical substance since the surface of the coating microneedle is coated with the medical substance. However, the needle remains, which may cause pollution.

In general, the melting-type microneedle or the coating microneedle according to the related art is applied to the even skin and thus, may not be readily applied to the gums having an irregularly curved shape within the mouth.

SUMMARY

Example embodiments provide a microneedle for dental material delivery that may be readily attached to the gums having a curved surface since a base of the microneedle is bendable to be in a shape corresponding to a shape of the gums within a mouth and a method of manufacturing the microneedle.

Example embodiments also provide a microneedle for dental material delivery that may coat the surface of a water-soluble microneedle containing a medical substance with a material in which an active ingredient is added and may deliver a fixed amount of active ingredients quickly when the microneedle is administered to the skin within a mouth and a method of manufacturing the microneedle.

Example embodiments also provide a microneedle for dental material delivery that may deliver a fixed amount of active ingredients within a relatively short period of time within a minimum number of administrations and a method of manufacturing the microneedle.

Example embodiments also provide a safe microneedle for dental material delivery in which the risk of pollution is absent after the dental treatment since the microneedle is manufactured to be water-soluble and the microneedle is partially or completely melted after being administered to the skin and a method of manufacturing the microneedle.

According to an aspect, there is a microneedle for dental material delivery, the microneedle including a needle body portion; an active ingredient coating portion configured to coat the surface of the needle body portion, and including an active ingredient transferred to the skin tissue within a mouth; and a base portion configured to couple with the needle body portion, and to bend along a skin shape within the mouth, wherein the base portion includes at least one of polyethylene (PE), polypropylene (PP), polytetrafluoroethylene (PTFE), polymethylmethacrylate (PMMA), ethylene vinyl acetate (EVA), polycaprolactone (PCL), polyurethane (PU), polyethylene terephthalate (PET), polyethylene glycol (PEG), polyvinyl alcohol (PVA), poly lactide (PLA), poly lactic-co-glycolic acid (PLGA), and polyglycolide (PGA).

The base portion may include at least one of polyethylene (PE), polypropylene (PP), polytetrafluoroethylene (PTFE), polymethylmethacrylate (PMMA), ethylene vinyl acetate (EVA), polyurethane (PU), polyethylene terephthalate (PET), polyethylene glycol (PEG), polyvinyl alcohol (PVA), poly lactide (PLA), and poly lactic-co-glycolic acid (PLGA), and polyglycolide (PGA), and polycaprolactone (PCL) at a weight (%) ratio of 1:9 to 5:5.

The base portion may include at least one of polyethylene (PE), polypropylene (PP), polytetrafluoroethylene (PTFE), polymethylmethacrylate (PMMA), ethylene vinyl acetate (EVA), polyurethane (PU), polyethylene terephthalate (PET), polyethylene glycol (PEG), polyvinyl alcohol (PVA), poly lactide (PLA), poly lactic-co-glycolic acid (PLGA), and polyglycolide (PGA), and polycaprolactone (PCL) at a weight (%) ratio of 1:9 or 2:8.

The base portion may include poly lactic-co-glycolic acid (PLGA) and polycaprolactone (PCL) at a weight (%) ratio of 1:9 to 5:5.

The needle body portion may include a viscous material and the active ingredient transferred to the skin tissue within the mouth.

The viscous material included in the needle body portion may include at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, turanose or lactulose and copolymer of monomers constituting the polymer, and cellulose.

The active ingredient coating portion may include the viscous material and the active ingredient transferred to the skin tissue within the mouth.

The viscous material included in the active ingredient coating portion may include at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, turanose or lactulose and copolymer of monomers constituting the polymer, and cellulose.

The viscous material may be included in each of the needle body portion and the active ingredient coating portion, and a solubility of the viscous material included in the active ingredient coating portion against the moisture may be greater than a solubility of the viscous material included in the needle body portion against the moisture.

When at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, and cyclodextrin that are included in the needle body portion and the active ingredient coating portion is a first viscous material, and when at least one of maltose, lactose, trehalose, cellobiose, isomaltose, turanose, and lactulose that are included in the needle body portion and the active ingredient coating portion is a second viscous material, a weight (%) ratio of the second viscous material over the first viscous material in the active ingredient coating portion may be greater than that of the second viscous material over the first viscous material in the needle body portion.

A weight (%) ratio of first viscous material:second viscous material:active ingredient in the needle body portion may be 1 to 7%:1 to 10%:1 to 10%.

A weight (%) ratio of first viscous material:second viscous material: active ingredient in the needle body portion may be 5%:5%:5%.

A weight (%) ratio of viscous material:active ingredient in the needle body portion may be within the range of 2:1 to 3:1.

A weight (%) ratio of first viscous material:second viscous material:active ingredient in the active ingredient coating portion may be 1 to 10%:1 to 30%:1 to 30%.

A weight (%) ratio of first viscous material:second viscous material:active ingredient in the active ingredient coating portion may be 3%:30%:30%.

A weight (%) ratio of viscous material:active ingredient in the active ingredient coating portion may be within the range of 1:1 to 1:2.

The first viscous material may be carboxymethyl cellulose (CMC), the second viscous material may be maltose, and the active ingredient may be lidocaine.

The active ingredient included in each of the needle body portion and the active ingredient coating portion may include at least one of lidocaine, mepivacaine, prilocaine, bupivacaine, etidocaine, articaine, procaine, propoxycaine, tetracaine, ropivacaine, butacaine, piperocaine, cocaine, benzocaine, chloroprocaine, proparacaine, and dyclonine.

According to another aspect, there is provided a microneedle for dental material delivery, the microneedle including a needle body portion formed using a water-soluble material; an active ingredient coating portion configured to coat the surface of the needle body portion, and including an active ingredient transferred to the skin tissue within a mouth; and a base portion configured to couple with the needle body portion and to bend along a shape of the gums, wherein the base portion is formed by mixing poly lactic-co-glycolic acid (PLGA) and polycaprolactone (PCL) at a weight (%) ratio of 1:9 to 5:5.

According to still another aspect, there is provided a method of manufacturing a microneedle, the method including manufacturing a needle body portion of the microneedle to be in a preset shape; forming a base portion by disposing a pellet on a mold on which the needle body portion of the microneedle is formed; separating the base portion and the needle body portion of the microneedle from the mold; preparing a coating solution in which a viscous material and an active ingredient that is transferred to the skin tissue within a mouth are mixed; coating the needle body portion of the microneedle with the coating solution; and drying the needle body portion of the microneedle in a room temperature.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION OF THE INVENTION

Figure 1:
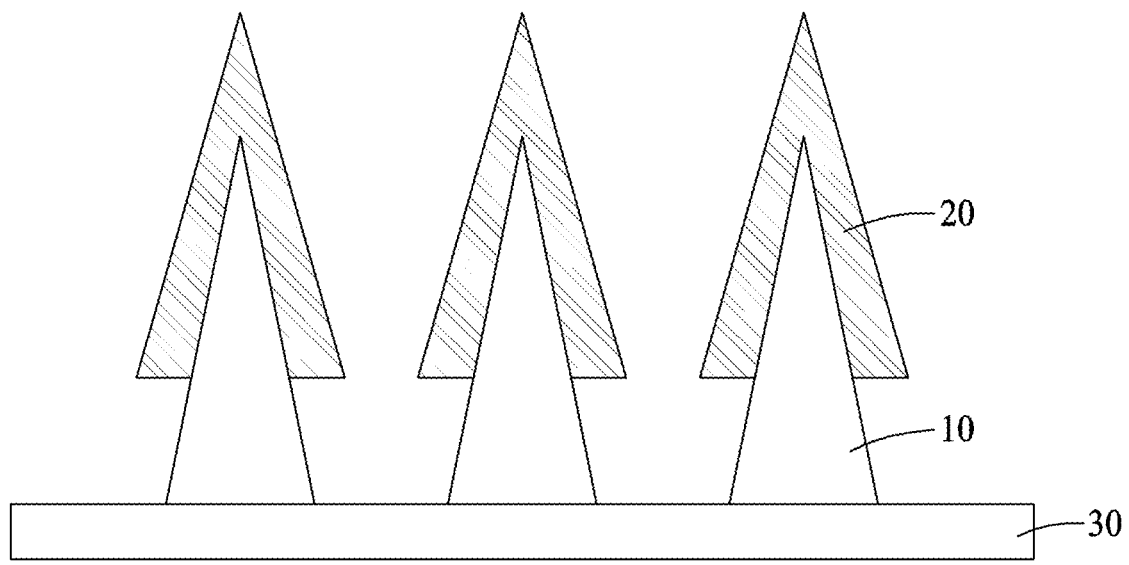
FIG. 1 is a cross-sectional view of a microneedle for dental material delivery according to example embodiments.

Hereinafter, example embodiments will be described with reference to the accompanying drawings. Herein, thicknesses of lines, sizes of constituent elements, etc., illustrated in the drawings, may be exaggerated for clarity and convenience of description. Further, terms described in the following are ones defined based on functions in the present disclosure and thus, may vary based on the intent of a user or an operator, or custom. Accordingly, the definition of such terms should be made based on the overall description disclosed in the present specification.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

FIG. 1 is a cross-sectional view of a microneedle for dental material delivery according to example embodiments.

Referring to FIG. 1, a microneedle 1 according to example embodiments may include a needle body portion 10, an active ingredient coating portion 20, and a base portion 30.

An end of the needle body portion 10 may be provided in a sharp conic shape. A shape of the needle body portion 10 is not particularly limited if the shape allows the penetration of a medical substance. The needle body portion 10 may be formed in a conic shape with the diameter of about 1 μm to about 100 μm.

The needle body portion 10 may be formed using a water-soluble material. In detail, when the microneedle 1 is applied to a melting-type microneedle, the needle body portion 10 may be formed using the mixture of a viscous material, such as carboxymethyl cellulose (CMC), having viscosity and an active ingredient, such as lidocaine, which is delivered to the mucous membrane of oral cavity. Here, the active ingredient indicates a concept that includes a dental medicine. In more detail, the needle body portion 10 may be prepared using the viscous material, such as carboxymethyl cellulose (CMC) and the like, and the active ingredient, such as lidocaine and the like, is added to the prepared needle body portion 10. As a result, the needle body portion 10 itself may contain the active ingredient.

Since the viscous material is included in the needle body portion 10, the mechanical strength of the needle body portion 10 may be enhanced.

As another example, when the microneedle 1 is applied to a coating microneedle, the needle body portion 10 may be formed using biodegradable polymer resin such as poly lactic acid (PLA) or poly lactic-co-glycolic acid (PLGA).

The viscous material included in the needle body portion 10 may include at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, turanose or lactulose and copolymer of monomers constituting the polymer, and cellulose.

Here, carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, and cyclodextrin may be referred to as a viscous material, for example, a first viscous material, having a relatively low water-solubility. In addition, maltose, lactose, trehalose, cellobiose, isomaltose, and turanose or lactulose may be a water-soluble material having a relatively high water-solubility and may be referred to as a viscous material, for example, a second viscous material, having a relatively high water-solubility since they act as the viscous material according to an increase in the concentration thereof.

Accordingly, a viscous material having a relatively low solubility, such as carboxymethyl cellulose (CMC), a viscous material having a relatively high solubility, such as maltose, which is a water-soluble material, however, acts as the viscous material according to an increase in the concentration thereof, and an active ingredient, such as lidocaine, may be included in the needle body portion 10 as primary components.

The needle body portion 10 may be manufactured by injecting and molding the mixture of the viscous material and the active ingredient into a mold M, or by injecting and molding biodegradable polymer resin into the mold M. A method of manufacturing the needle body portion 10 and materials of the mold M will be further described below.

The surface of the needle body portion 10 may be coated with the active ingredient coating portion 20. The active ingredient coating portion 20 may be formed using a material in which the viscous materials, such as carboxymethyl cellulose (CMC), maltose, and the like, and the active ingredient, such as lidocaine and the like, are mixed at a preset ratio.

The viscous materials included in the active ingredient coating portion 20 may include a viscous material having a relatively high water-solubility, such as lactose, trehalose, cellobiose, isomaltose, turanose or lactulose, and the like, in addition to maltose, and may also include a viscous material having a relatively low water-solubility, such as carboxymethyl cellulose (CMC) and the like.

Compared to the needle body portion 10, in the active ingredient coating portion 20, a ratio of the viscous material having the relatively high water-solubility, such as maltose and the like, may be significantly greater than a ratio of the viscous material having the relatively low water-solubility such as carboxymethyl cellulose (CMC) and the like.

As described above, since the active ingredient, for example, dental medicine, is distributed over the surface of the needle body portion 10, that is, the active ingredient coating portion 20, a fixed about of active ingredients, for example, the dental medicine, may be delivered to the mucous membrane of oral cavity or the inside of the gums. In addition, since the active ingredient is included in the active ingredient coating portion 20 and also included in the needle body portion 10 having a volume greater than a volume of the active ingredient coating portion 20, a large amount of active ingredients may be delivered and the active ingredient may be delivered over a relatively long period of time.

Accordingly, a minimum amount of active ingredients that is to be delivered to the mucous membrane of oral cavity or the inside of the gums quickly may be included in the active ingredient coating portion 20 and thereby be quickly delivered to the mucous membrane of oral cavity or the inside of the gums. A remaining amount of active ingredients may be included in the needle body portion 10.

A process of coating and drying the surface of the needle body portion 10 with the active ingredient coating portion 20 will be described below.

A viscous material, such as maltose and the like, included in the active ingredient coating portion 20 has a relatively high solubility, that is, a high soluble rate, compared to a viscous material, such as CMC and the like, included in the needle body portion 10. Thus, once the microneedle 1 is applied to the gums within the mouth, the active ingredient, for example, lidocaine, included in the active ingredient coating portion 20 may be quickly delivered to the gums or the mucous membrane of oral cavity compared to the active ingredient included in the needle body portion 10.

A viscous material having a relatively high solubility, such as maltose, lactose, trehalose, cellobiose, isomaltose, and turanose or lactulose, and the like, may be included in the needle body portion 10 as well as the active ingredient coating portion 20. However, since a ratio of the viscous material included in the needle body portion 10 is significantly less than a ratio of the viscous material included in the active ingredient coating portion 20, the active ingredient included in the active ingredient coating portion 20 may be delivered to the gums or the mucous membrane of oral cavity quickly compared to the active ingredient included in the needle body portion 10.

According to an increase in the ratio of the viscous material having the relatively high solubility, such as maltose and the like, a delivery rate of active ingredients may increase.

For example, when a ratio of a viscous material having a relatively high solubility, such as maltose and the like, included in the needle body portion 10 is about 5%, a ratio of a viscous material having a relatively high solubility, such as maltose and the like, included in the active ingredient coating portion 20 may be about 30%. Accordingly, by adjusting an amount of active ingredients to be included in the active ingredient coating portion 20 and an amount of active ingredients to be included in the needle body portion 10, it is possible to adjust a rate at which the active ingredient is delivered to the gums or the mucous membrane of oral cavity. For example, to increase a rate at which the active ingredient, such as lidocaine and the like, is delivered to the gums or the mucous membrane, an amount of active ingredients to be included in the active ingredient coating portion 20 may be adjusted to be greater than an amount of active ingredients to be included in the needle body portion 10. On the contrary, to relatively decrease the delivery rate of active ingredients, an amount of active ingredients to be included in the active ingredient coating portion 20 may be adjusted to be less than an amount of active ingredients to be included in the needle body portion 10.

Also, the active ingredient included in each of the active ingredient coating portion 20 and the needle body portion 10 may be dental medicine. The active ingredient may include at least one of lidocaine, mepivacaine, prilocaine, bupivacaine, etidocaine, articaine, procaine, propoxycaine, tetracaine, ropivacaine, butacaine, piperocaine, cocaine, benzocaine, chloroprocaine, proparacaine, and dyclonine.

A ratio of a viscous material having a relatively low solubility, a viscous material having a relatively high solubility, and an active ingredient in the needle body portion 10, more precisely, at the tip of the needle body portion 10 may be 5 weight %:5 weight %:5 weight %. For example, carboxymethyl cellulose (CMC):maltose:lidocaine may be included at the tip of the needle body portion 10 at a weight (%) ratio of 5%:5%:5%.

Accordingly, in the case of the needle body portion 10, a ratio of viscous material:active ingredient may be within the range of 10:0 to 1:9, desirably, within the range of 2:1 to 3:1.

Also, a ratio of a viscous material having a relatively low solubility, a viscous material having a relatively high solubility, and an active ingredient in the active ingredient coating portion 20 may be 5 weight %:30 weight %:30 weight %. For example, hydroxypropyl methyl cellulose (HPMC):maltose:lidocaine may be included in the active ingredient coating portion 20 at a weight (%) ratio of 5%:30%:30%.

Accordingly, in the case of the active ingredient coating portion 20, a ratio of viscous material:active ingredient may be within the range of 9:1 to 1:9, desirably, within the range of 1:1 to 1:2. The base portion 30 may be coupled with the needle body portion 10 and may be formed to bend along a shape of the gingival, that is, the gums. In detail, the base portion 30 may be formed using a flexible material to flexibly bend along the curve of the gingiva.

The base portion 30 may include at least one of polyethylene (PE), polypropylene (PP), polytetrafluoroethylene (PTFE), polymethylmethacrylate (PMMA), ethylene vinyl acetate (EVA), polycaprolactone (PCL), polyurethane (PU), polyethylene terephthalate (PET), polyethylene glycol (PEG), polyvinyl alcohol (PVA), poly lactide (PLA), poly lactic-co-glycolic acid (PLGA), and polyglycolide (PGA).

The base portion 30 may include another polymer, aside from polycaprolactone (PCL), and polycaprolactone (PCL) at a weight (%) ratio of 1:9 to 5:5, desirably, at a weight ratio of 1:9 or 2:8.

That is, the base portion 30 may include another polymer, for example, one of polyethylene (PE), polypropylene (PP), polytetrafluoroethylene (PTFE), polymethylmethacrylate (PMMA), ethylene vinyl acetate (EVA), polyurethane (PU), polyethylene terephthalate (PET), polyethylene glycol (PEG), polyvinyl alcohol (PVA), poly lactide (PLA), poly lactic-co-glycolic acid (PLGA), and polyglycolide (PGA), and polycaprolactone (PCL) at a weight (%) ratio of 1:9 to 5:5, desirably, at a weight (%) ratio of 1:9 or 2:8.

For example, the base portion 30 may be formed to have the effect of two materials by mixing poly lactic-co-glycolic acid (PLGA) and polycaprolactone (PCL) at a weight (%) ratio of 1:9 to 5:5. Here, PLGA may be fragile, however, capable of maintaining the mechanical strength and PCL may have a flexible property.

Alternatively, the base portion 30 may be formed using only polycaprolactone (PCL).

A process of coupling the base portion 30 and the needle body portion 10 will be further described below.

Figure 2:
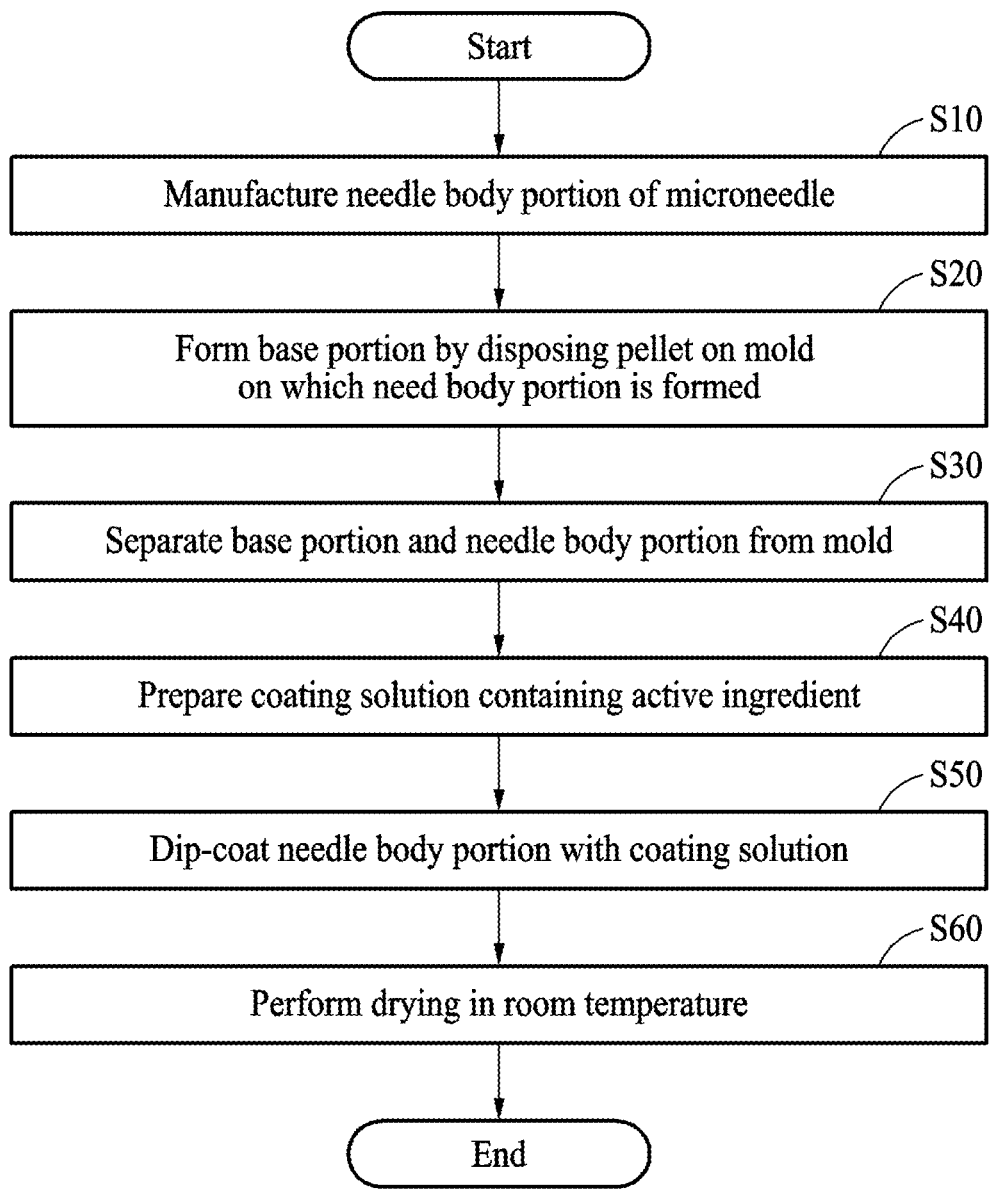
FIG. 2 is a flowchart illustrating a process of a method of manufacturing a microneedle for dental material delivery according to example embodiments.

FIG. 2 is a flowchart illustrating a process of a method of manufacturing a microneedle for dental material delivery according to example embodiments.

Referring to FIG. 2, to manufacture the microneedle 1 for dental material delivery according to example embodiments, the needle body portion 10 of the microneedle 1 may be manufactured to be in a preset shape in operation S10. In operation S20, the base portion 30 may be formed by disposing a pellet on the mold M in which the needle body portion 10 of the microneedle 1 is formed. In operation S30, the base portion 30 and the needle body portion 10 may be separate from the mold M. In operation S40, a coating solution of the active ingredient coating portion 20 used to coat the needle body portion 10 may be prepared. In operation S50, the needle body portion 10 may be dip-coated with the coating solution of the active ingredient coating portion 20. In operation S60, the microneedle 1 coated with the coating solution of the active ingredient coating portion 20 may be dried in a room temperature.

Hereinafter, each operation will be described with reference to the accompanying drawings.

Figure 3:
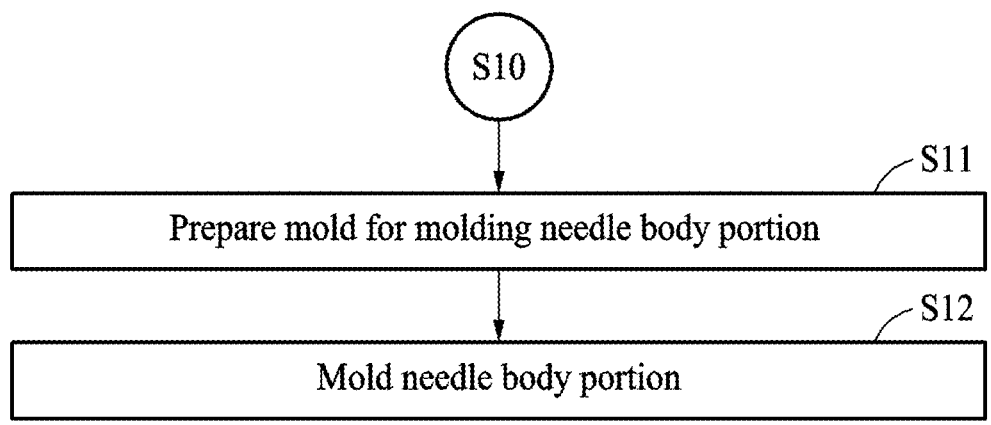
FIG. 3 is a flowchart illustrating an operation of manufacturing a needle body portion of a microneedle for dental material delivery according to example embodiments.
Figure 4A:
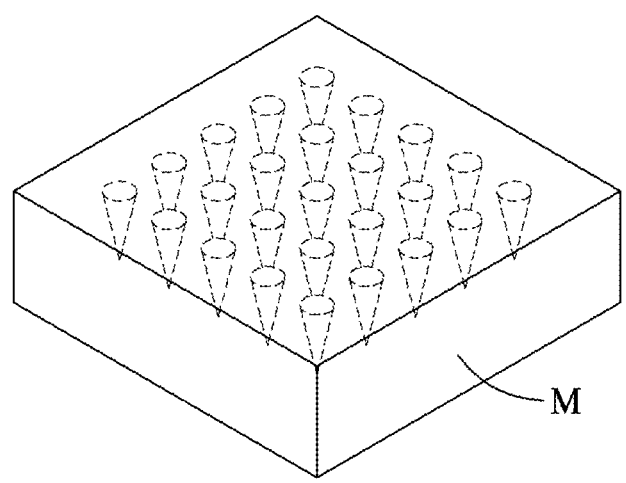
FIG. 4A is a perspective view illustrating a mold for manufacturing a microneedle according to example embodiments.
Figure 4B:
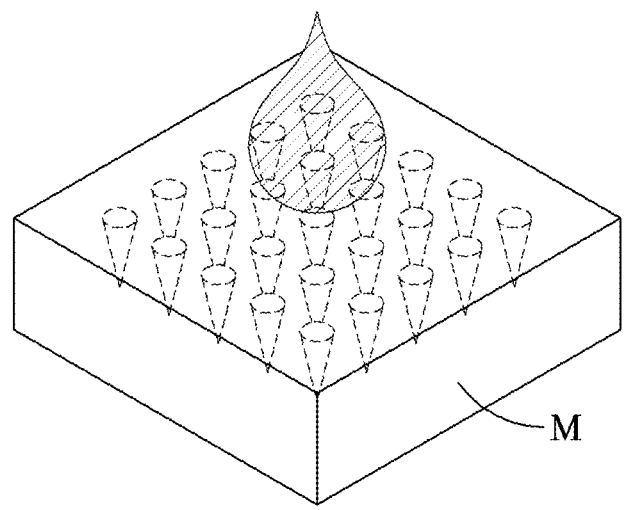
FIG. 4B is a perspective view illustrating a state in which a raw material for manufacturing the microneedle or biodegradable polymer resin is melted and in this state, is applied to the mold of FIG. 4A.
Figure 4C:
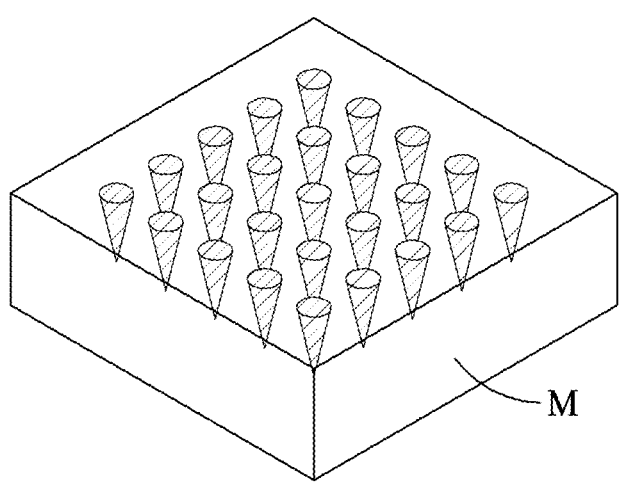
FIG. 4C illustrates a perspective view illustrating a state of drying the raw material or the biodegradable polymer resin remaining on the surface of the mold of FIG. 4B.

FIG. 3 is a flowchart illustrating an operation of manufacturing a needle body portion of a microneedle for dental material delivery according to example embodiments, FIG. 4A is a perspective view illustrating a mold for manufacturing a microneedle according to example embodiments, FIG. 4B is a perspective view illustrating a state in which a raw material for manufacturing the microneedle or biodegradable polymer resin is melted and in this state, is applied to the mold of FIG. 4A, and FIG. 4C illustrates a perspective view illustrating a state of drying the raw material or the biodegradable polymer resin remaining on the surface of the mold of FIG. 4B.

Referring to FIGS. 3 and 4, the needle body portion 10 of the microneedle 1 may be manufactured based on molding. Operation S10 of manufacturing the needle body portion 10 of the microneedle 1 in the preset shape may include operation S11 of preparing the mold M for molding the needle body portion 10 and operation S12 of molding the needle body portion 10.

As described above, the needle body portion 10 may include at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, turanose or lactulose and copolymer of monomers constituting the polymer, and cellulose.

Referring to FIG. 4A, a plurality of grooves in a conic shape may be formed on the mold M to manufacture an end of the needle body portion 10 in a sharp shape.

Here, the mold M may be a structure that includes at least one of polydimethylsiloxane (PDMS), a type of polymer used for the mold, polyurethane, metal, an aluminum biocompatible material, water-soluble polymer, fat-soluble polymer, and amphiphilic polymer. The fat-soluble polymer and the amphiphilic polymer may include at least one of hydroxypropyl cellulose (HPC), hydroxypropyl methyl cellulose (HPMC), polycaprolactone (PCL), polyglycolide (PGA), polylactic acid (PLA), poly lactic-co-glycolic acid (PLGA), poly vinyl pyrrolidone (PVP), polyethylene glycol (PEG), poly ethylene oxide (PEO), poly propylene oxide (PPO), poly vinyl methyl ether (PVME), PMA (poly (methyl) acrylate)s, propylene glycol, poly (ester amide), poly (butyric acid), acrylamide (acrylic amide), acrylic acid, hyaluronic acid (HA), and gelatin.

In detail, in operation S12, inside bubbles may be removed by filling the PDMS mold M with a solution in which a viscous material, such as carboxymethyl cellulose (CMC) and the like, and an active ingredient transferred to the skin tissue within the mouth are melted and by performing vacuum processing.

In more detail, a solution in which 1 to 7 weight %, desirably, 5 weight %, of a first viscous material, such as carboxymethyl cellulose (CMC) and the like, 1 to 10 weight %, desirably, 5 weight %, of a second viscous material, such as maltose and the like, and 1 to 10 weight %, desirably, 5 weight %, of an active ingredient, such as lidocaine and the like, are melted in the deionized water may fill in a tip portion, for example, a recessed portion of the PDMS mold.

Accordingly, in the case of the needle body portion 10, a ratio of viscous material:active ingredient may be within the range of 10:0 to 1:9, desirably, within the range of 2:1 to 3:1.

Referring to FIGS. 4B and 4C, the needle body portion 10 of the microneedle 1 may be manufactured by remaining only a solution received in conic grooves formed on the mold M, by removing a solution remaining on the surface of the mold M, and by naturally drying the solution received in the conic grooves formed on the mold M.

In more detail, the solution received in the conic grooves formed on the mold M may be dried in a room temperature of, for example, about 25° C. for about 1 hour and then may be dried in the oven of about 70° C. for about 1 hour.

Accordingly, when the natural drying is performed with remaining the solution received in the conic grooves formed on the mold M, the needle body portion 10 may be formed on each of the plurality of grooves on the mold M as illustrated in FIG. 4C.

Figure 5:
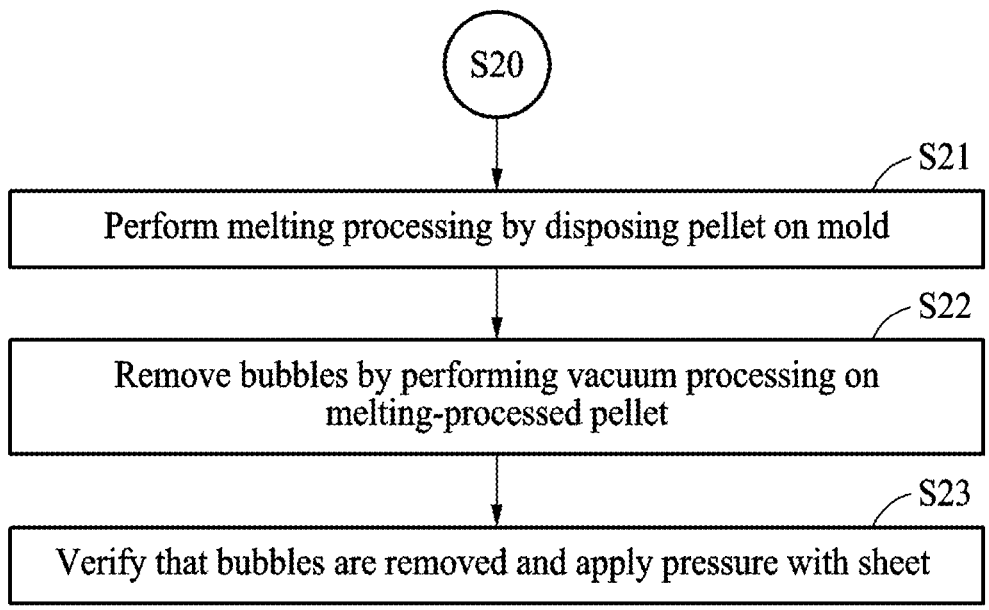
FIG. 5 is a flowchart illustrating an operation of forming a base portion on a mold on which the needle body portion of the microneedle is formed according to example embodiments.
Figure 6A:
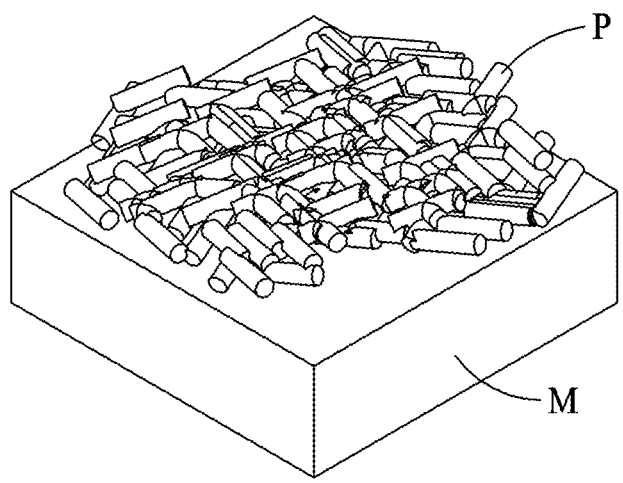
FIG. 6A is a perspective view illustrating a process of performing melting processing by disposing a pellet on a mold on which a needle body portion of a microneedle is formed according to example embodiments.
Figure 6B:
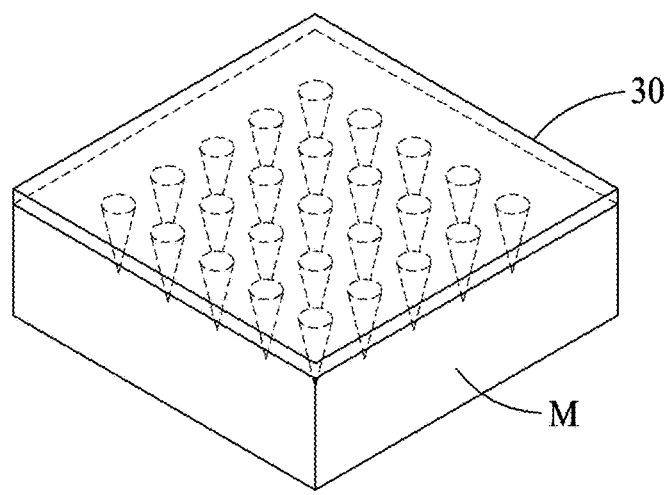
FIG. 6B is a perspective view illustrating a process of forming a base portion by removing bubbles through vacuum processing of the melting processed pellet of FIG. 6A and applying a pressure with a sheet pressing machine.
Figure 7:
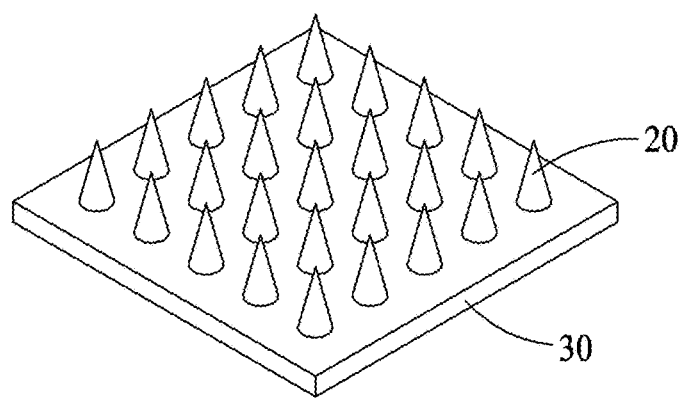
FIG. 7 is a perspective view illustrating a state in which a needle body portion and a base portion of a microneedle are separate from a mold according to example embodiments.

FIG. 5 is a flowchart illustrating an operation of forming a base portion on a mold on which a needle body portion of a microneedle is formed according to example embodiments, FIG. 6A is a perspective view illustrating a process of performing melting processing by disposing a pellet on a mold on which a needle body portion of a microneedle is formed according to example embodiments, FIG. 6B is a perspective view illustrating a process of forming a base portion by removing bubbles through vacuum processing of the melting processed pellet of FIG. 6A and applying a pressure with a sheet pressing machine, and FIG. 7 is a perspective view illustrating a state in which a needle body portion and a base portion of a microneedle are separate from a mold according to example embodiments.

Referring to FIGS. 5 through 7, operation S20 of forming the base portion 30 by disposing a pellet on the mold M on which the needle body portion 10 of the microneedle 1 is formed may include operation S21 of performing melting processing by disposing the pellet P on the mold M, operation S22 of removing bubbles by performing vacuum processing on the melting-processed pellet P, and operation S23 of verifying that the bubbles are removed and applying a pressure with a sheet pressing machine.

Referring to FIG. 6A, the pellet P may be a resin particle for molding used to form the base portion 30, and the pellet P may be disposed on the mold M on which the needle body portion 10 is formed.

The pellet P may include at least one of polyethylene (PE), polypropylene (PP), polytetrafluoroethylene (PTFE), polymethylmethacrylate (PMMA), ethylene vinyl acetate (EVA), polycaprolactone (PCL), polyurethane (PU), polyethylene terephthalate (PET), polyethylene glycol (PEG), polyvinyl alcohol (PVA), poly lactide (PLA), poly lactic-co-glycolic acid (PLGA), and polyglycolide (PGA).

The pellet P may include another polymer, aside from polycaprolactone (PCL), and polycaprolactone (PCL) at a weight (%) ratio of 1:9 to 5:5, desirably, at a weight (%) ratio of 1:9 or 2:8.

That is, the pellet P may include another polymer, for example, one of polyethylene (PE), polypropylene (PP), polytetrafluoroethylene (PTFE), polymethylmethacrylate (PMMA), ethylene vinyl acetate (EVA), polyurethane (PU), polyethylene terephthalate (PET), polyethylene glycol (PEG), polyvinyl alcohol (PVA), poly lactide (PLA), poly lactic-co-glycolic acid (PLGA), and polyglycolide (PGA), and polycaprolactone (PCL) at a weight (%) ratio of 1:9 to 5:5, desirably, at the weight (%) ratio of 1:9 or 2:8.

For example, the pellet P may be prepared by mixing poly lactic-co-glycolic acid (PLGA) and polycaprolactone (PCL) at a weight (%) ratio of 1:9 to 5:5. Here, Here, PLGA may be fragile, however, capable of maintaining the mechanical strength and PCL may have a flexible property. Accordingly, the base portion 30 may be formed to have the effect of two materials.

Alternatively, the pellet P may be formed using only polycaprolactone (PCL) that has a flexible property.

Melting processing may be performed on the pellet P disposed on the mold M within the temperature range of about 70 to about 150° C. For example, melting processing may be performed on the pellet P disposed on the mold M in a vacuum oven of about 60 to 100° C.

Bubbles may be removed from the melting processed pellet P through vacuum processing. When the bubbles are verified to be removed, the base portion 30 may be formed by applying a pressure with a 500 g sheet pressing machine. By using the sheet pressing machine, the base portion 30 may be uniformly formed on the mold M, and the needle body portion 10 received in the groove of the mold M and the base portion 30 may be coupled to each other.

When the base portion 30 and the needle body portion 10 are completely coupled by forming the base portion 30 on the mold M, the base portion 30 and the needle body portion 10 may be separate from the mold M in operation S30. As illustrated in FIG. 7, a plurality of needle body portions 10 may be formed in a conic shape on the base portion 30.

Figure 8:
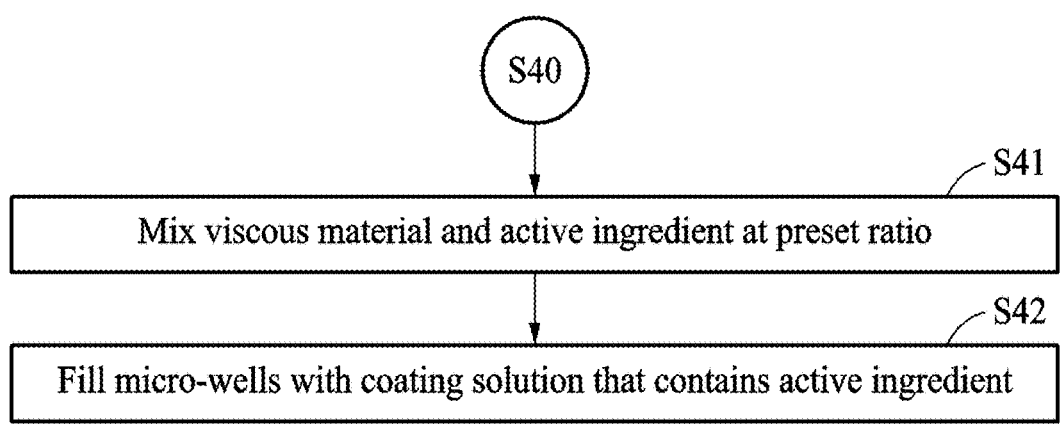
FIG. 8 is a flowchart illustrating an operation of preparing a coating solution containing an active ingredient of a microneedle for dental material delivery according to example embodiments.
Figure 9:
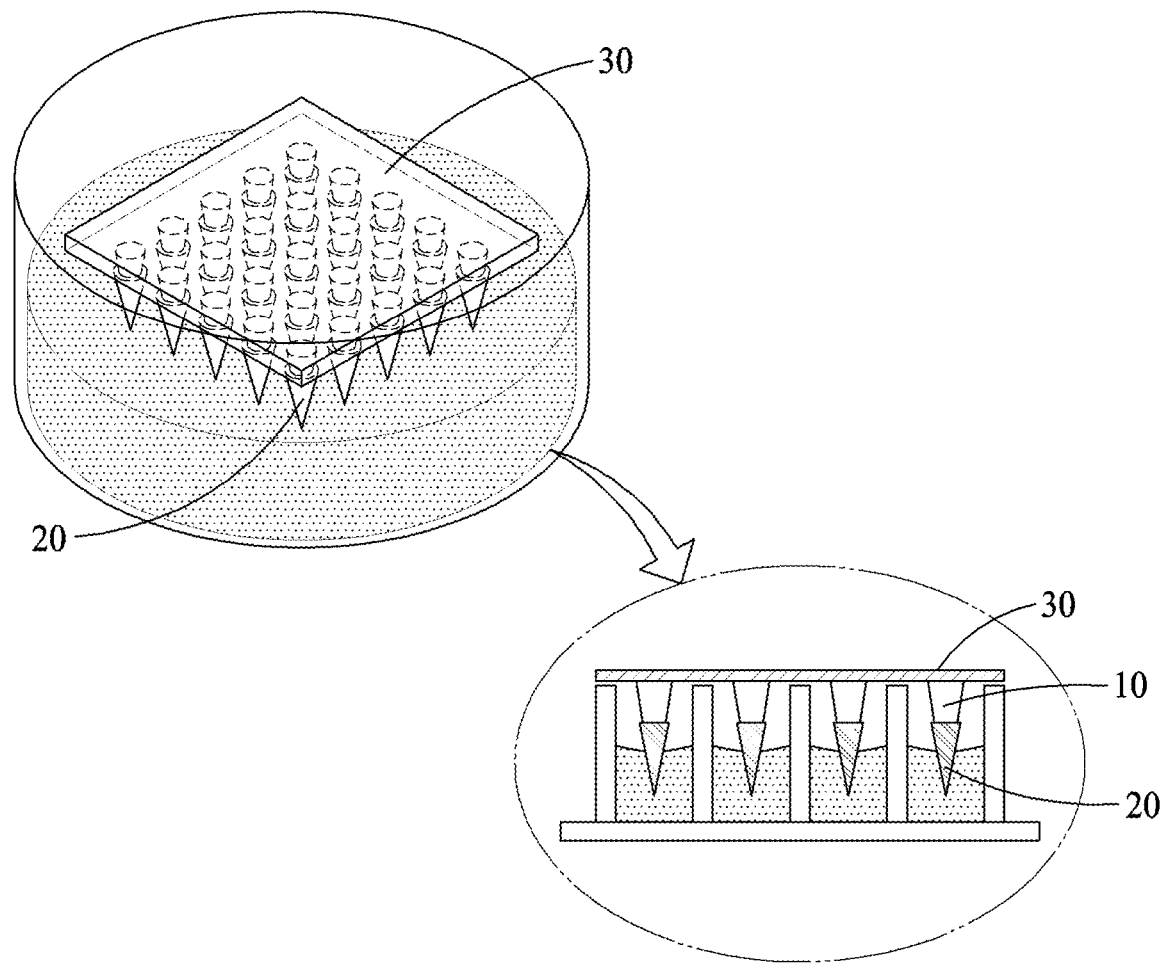
FIG. 9 illustrates a state in which a needle body portion of a microneedle is dipped into a coating solution containing an active ingredient according to example embodiments.
Figure 10:
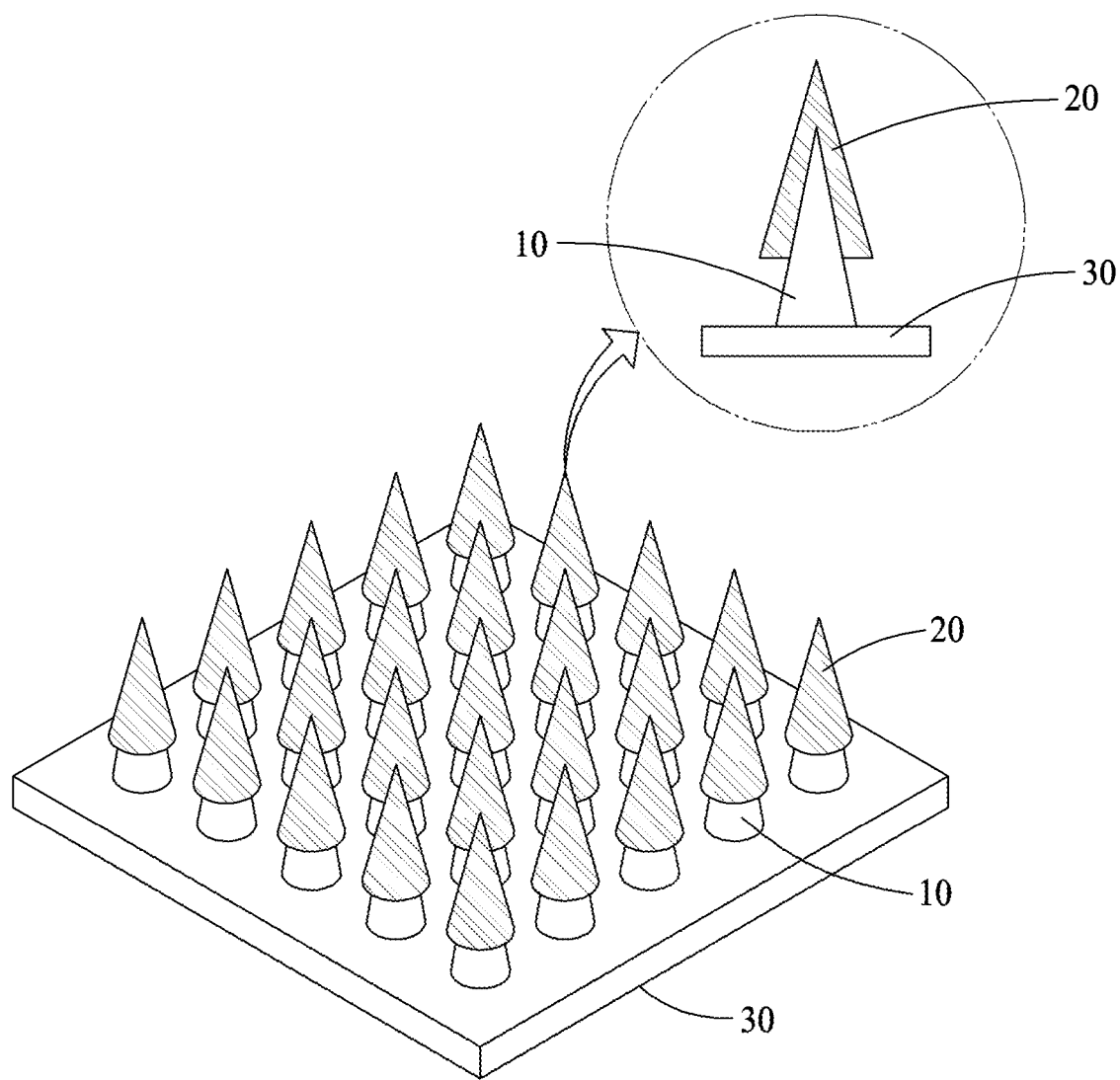
FIG. 10 illustrates an operation of drying a microneedle coated with an active ingredient coating portion in a room temperature according to example embodiments.

FIG. 8 is a flowchart illustrating an operation of preparing a coating solution containing an active ingredient of a microneedle for dental material delivery according to example embodiments, FIG. 9 illustrates a state in which a needle body portion of a microneedle is dipped into a coating solution containing an active ingredient according to example embodiments, and FIG. 10 illustrates an operation of drying a microneedle coated with an active ingredient coating portion in a room temperature according to example embodiments.

Referring to FIGS. 8 through 10, operation S40 of preparing a coating solution of the active ingredient coating portion 20 used to coat the needle body portion 10 may include operation S41 of mixing a viscous material and an active ingredient at a preset ratio and operation S42 of filling micro-wells with the coating solution that contains the active ingredient.

A viscous material to be mixed with an active ingredient during a process of preparing the coating solution of the active ingredient coating portion 20 may include at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide polyethylene oxide), polyvinylpyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, turanose or lactulose and copolymer of monomers constituting the polymer, and cellulose.

In detail, a solution in which 1 to 10 weight %, desirably, 3%, of a first viscous material, such as carboxymethyl cellulose (CMC) and the like, 1 to 30 weight %, desirably, 30%, of a second viscous material, such as maltose and the like, and 1 to 30 weight %, desirably, 30%, of an active ingredient, such as lidocaine and the like, are melted in the deionized water may fill in the micro wells and the needle body portion 30 of the microneedle 1 may be dip-coated.

Accordingly, in the case of the active ingredient coating portion 20, a ratio of viscous material:active ingredient may be within the range of 9:1 to 1:9, desirably, within the range of 1:1 to 1:2.

Here, as described above, the active ingredient may include at least one of lidocaine, mepivacaine, prilocaine, bupivacaine, etidocaine, articaine, procaine, propoxycaine, tetracaine, ropivacaine, butacaine, piperocaine, cocaine, benzocaine, chloroprocaine, proparacaine, and dyclonine.

After dipping and coating the needle body portion 10 manufactured using the coating solution containing the active ingredient through molding into the coating solution that is prepared by mixing the viscous materials and the active ingredient in operation S50, the needle body portion 10 coated with the coating solution may be dried in a room temperature in operation S60.

Figure 11:
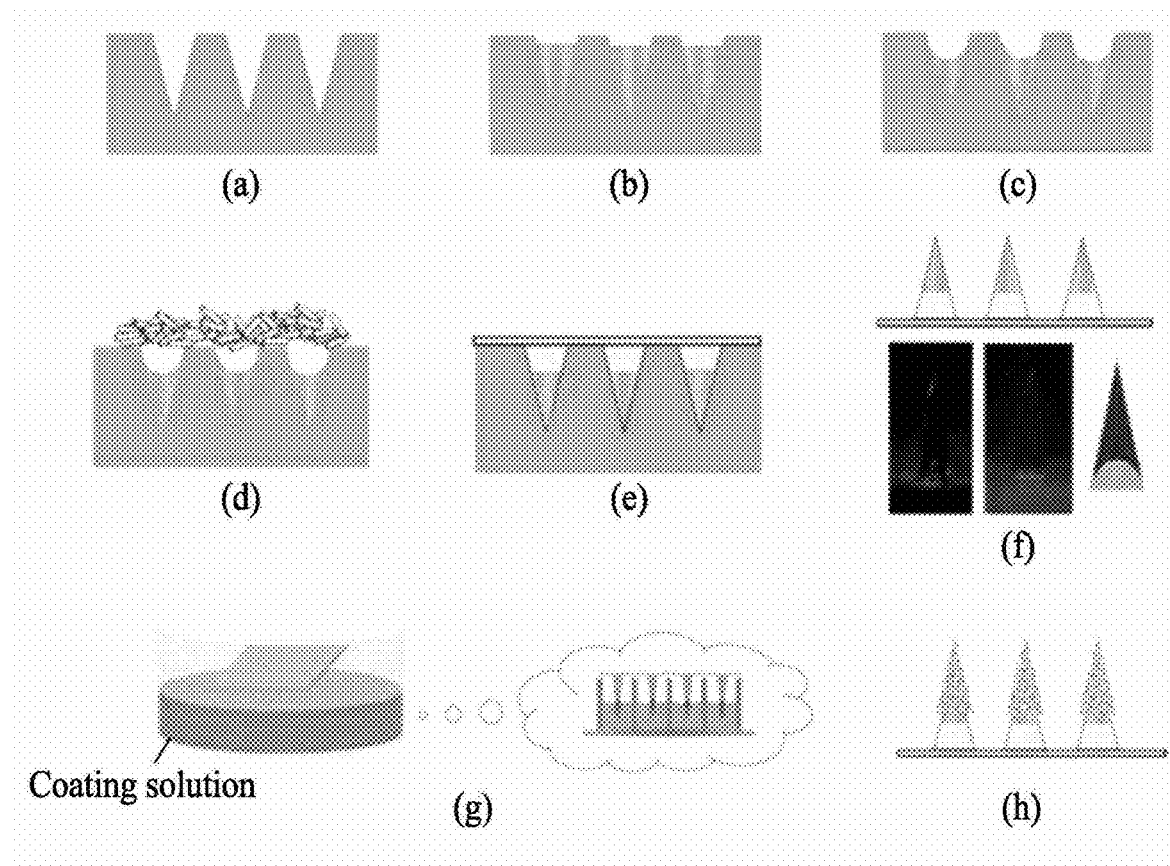
FIG. 11 sequentially illustrates a process of manufacturing a microneedle for dental material delivery according to example embodiments.

FIG. 11 sequentially illustrates a process of manufacturing a microneedle for dental material delivery according to example embodiments.

Hereinafter, the embodiment will be described with reference to FIG. 11.

(1) Referring to (a) of FIG. 11, the PDMS mold is prepared.

(2) Referring to (b) of FIG. 11, after filling a tip portion, for example, a recessed portion of the PDMS mold with a solution in which 1 to 7 weight %, desirably, 5%, of carboxymethyl cellulose (CMC), 1 to 10 weight %, desirably, 5%, of maltose, and 1 to 10 weight %, desirably, 5%, of an active ingredient, such as lidocaine, are melted in the deionized water, the PDMS mold is dried in a room temperature for about 1 hour and then dried in an oven of about 70° C. for about 1 hour. The actual test was implemented under the condition of CMC 5%+maltose 5%+lidocaine 5%. (c) of FIG. 11 illustrates a shape of the tip portion of the needle body portion filled in the PDMS mold after the drying process is completed.

(3) Referring to (d) of FIG. 11, the polycaprolactone (PCL) pellet is disposed on the mold, for example, a base portion, and bubbles are removed through decompression and compression in the vacuum oven of about 60 to 100° C. In the actual test, when the base has a size of 0.7 cm×0.7 cm, 0.8 g of the polycaprolactone (PCL) pellet was disposed on the base and bubbles were removed in the vacuum oven of about 70° C.

(4) Referring to (e) of FIG. 11, when the bubbles are removed, the pellet is taken out of the vacuum oven and is pressurized with a steel plate of 500 g and cooled.

(5) Referring to (f) of FIG. 11, the needle body portion of the microneedle is completed by taking out the cooled needle body portion of the microneedle.

(6) Referring to (g) of FIG. 11, a solution in which 1 to 10 weight %, desirably, 3%, of carboxymethyl cellulose (CMC), 1 to 30 weight %, desirably, 30%, of maltose, and 1 to 30 weight %, desirably, 30%, of an active ingredient, such as lidocaine, are melted in the deionized water fills in the micro-wells and the needle body portion of the microneedle is dip-coated. The actual test was implemented under the condition of CMC 3%+maltose 30%+lidocaine 30%.

(7) (h) of FIG. 11 illustrates the completed microneedle for dental material delivery, for example, a flexible microneedle for oral local anesthesia.

TABLE 1

| | Conventional coating microneedle | Proposed oral flexible microneedle |
| --- | --- | --- |
| Appl. | PLA or PLGA corresponding to an constituent element of the conventional coating microneedle has excellent mechanical strength, however, is not readily applicable to the curve of the gums due to lack of flexibility, | PCL has relatively weak mechanical strength and thus, is suitable for the gums in which a horny layer is barely present rater than being applied to the skin with the horny layer. Flexibly bendable and thus, suitable for the curve of the gums. |
| Pain level | When an edge portion of a base tip of the microneedle reaches the gums first, a patient experiences relatively great pain. The existing coating microneedle gives relatively great pain when a tip of a needle touches the gums. When applying the microneedle to the gums, it may cause relatively great pain. | Due to its flexibility, a patient may barely feel pain although an edge portion of a base tip reaches the gums first. When inserting the needle with the same length, it may barely cause pain. |

Table 1 shows a comparison between the conventional coating microneedle and the proposed microneedle for dental material delivery according to example embodiments.

Figure 12A:
FIG. 12A illustrates a shape of a microneedle applicable to a curved surface of the facial skin or the hand skin according to the related art.
Figure 12B:
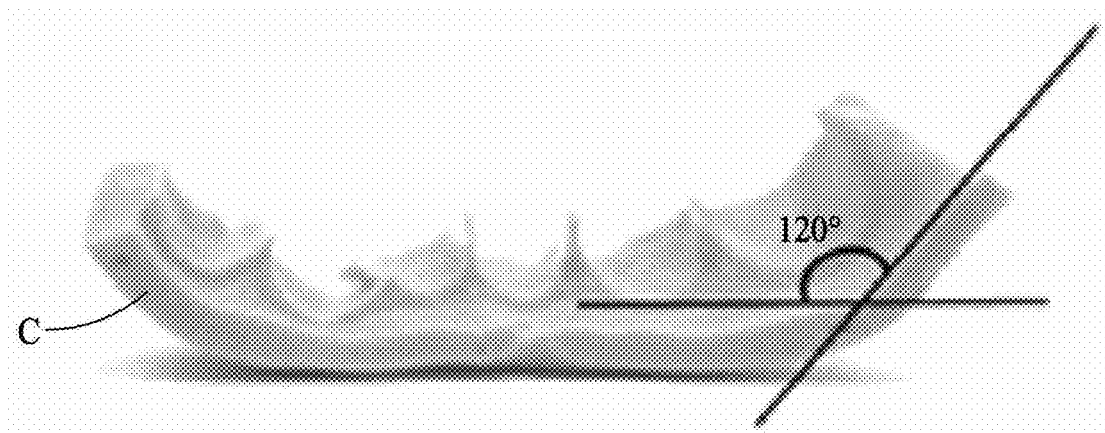
FIG. 12B illustrates a shape of a microneedle flexibly bendable along the curve of the gums according to example embodiments.
Figure 13A:
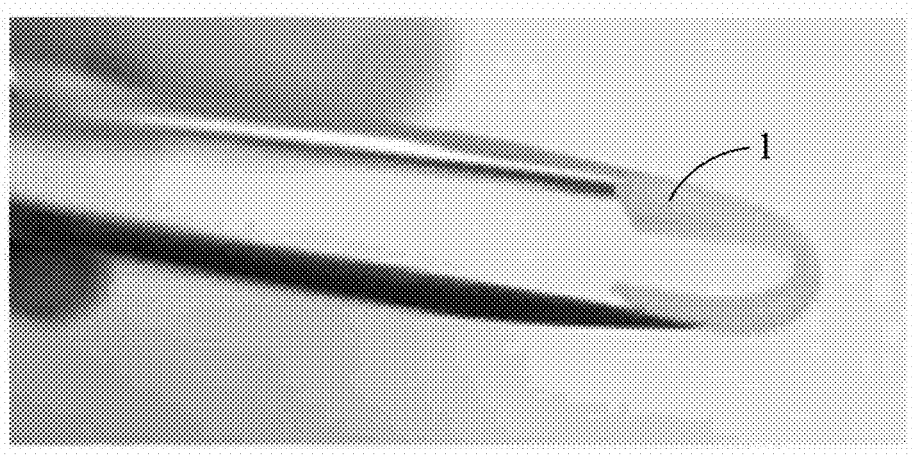
FIG. 13A illustrates a shape of a flexibly bending microneedle according to example embodiments.
Figure 13B:
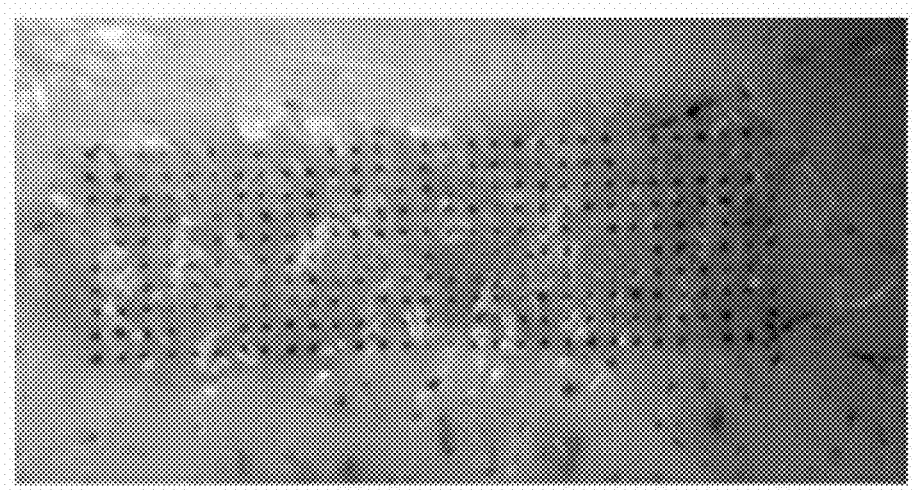
FIG. 13B illustrates mechanical strength of the microneedle of FIG. 13A.

FIG. 12A illustrates a shape of a microneedle applicable to a curved surface of the facial skin or the hand skin according to the related art, FIG. 12B illustrates a shape of a microneedle flexibly bendable along the curve of the gums according to example embodiments, FIG. 13A illustrates a shape of a flexibly bending microneedle according to example embodiments, and FIG. 13B illustrates mechanical strength of the microneedle of FIG. 13A.

Referring to FIGS. 12B and 13, the microneedle 1 according to example embodiments may be manufactured to flexibly bend along the curved surface of the gingiva.

Referring to FIG. 12A, the microneedle according to the related art may use a needle S along the curved surface of the facial skin or the hand skin, and may be attached along the curved surface of the facial skin or the hand skin to deliver an active ingredient such as a medical substance. The needle S according to the related art may be formed to be bendable within the range of about 160 to about 180° in order to be flexibly attached along the curved surface of the facial skin or the hand skin.

On the contrary, since the microneedle 1 according to example embodiments may bend at a relatively greater angle compared to the microneedle S according to the related art, the microneedle 1 may be formed to flexibly bend along the ridge C of the gingiva, that is, the gums. For example, the microneedle 1 may be manufactured in any shape and may be formed to bend within the range of about 100 to about 165° along the curve of the gums.

According to example embodiments, the microneedle 1 may be formed using a flexible material suitable for the curve of the gums and thus, may further effectively deliver dental medicine to the inside of the gums.

FIG. 13B illustrates the mechanical strength of the microneedle 1 according to example embodiments. Referring to FIG. 13B, since a viscous material such as carboxymethyl cellulose (CMC) is included in the needle body portion 10, the mechanical strength of the needle body portion 10 may be enhanced and the microneedle 1 may be easily inserted into the gums and deliver the dental medicine.

Figure 14:
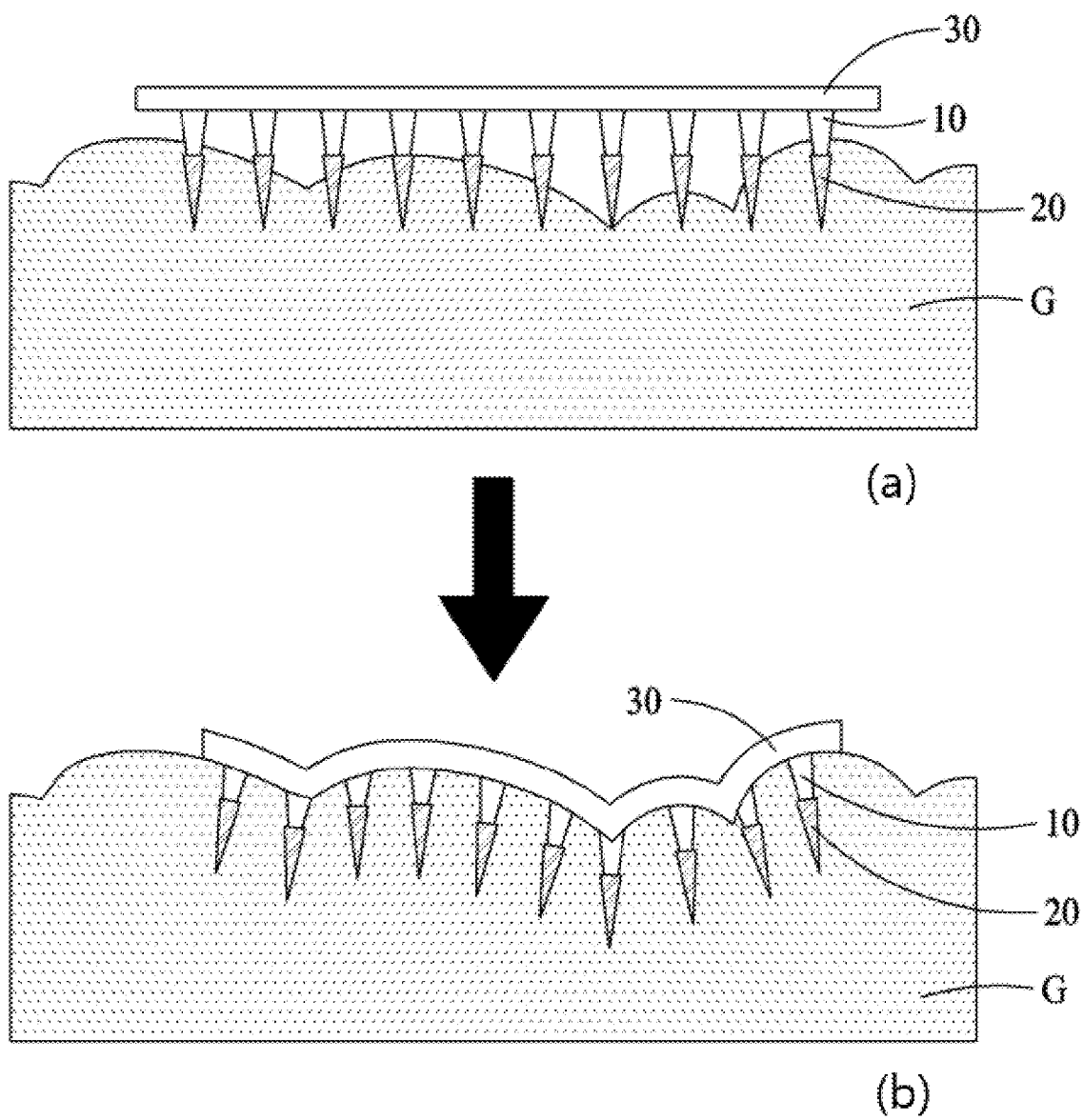
FIG. 14 illustrates a shape of a microneedle being inserted into the gums and a shape of the microneedle being bent flexibly and inserted along the curved surface of the gums, respectively, according to example embodiments.

FIG. 14 illustrate a shape of a microneedle being inserted into the gums and a shape of the microneedle being bent flexibly and inserted along the curved surface of the gums, respectively, according to example embodiments.

Referring to (a) and (b) of FIG. 14, the microneedle 1 may be formed to flexibly bend and be inserted along the curved surface of the gums, that is, the gingiva.

Referring to (a) of FIG. 14, the base portion 30 may maintain a flat state until the microneedle 1 is completely inserted into the gingiva G. The needle body portions 10 of the microneedle 1 may be inserted along the gingiva G from ends of the active ingredient coating portions 20.

Referring to (b) of FIG. 14, once the needle body portions 10 are completely inserted along the gingiva G, the base portion 30 may flexibly bend along a shape of the curved surface of the gingiva G. In particular, the microneedle 1 may be formed as a coating microneedle, and may be formed using a flexible material so that the base portion 30 may be effectively adsorbed along an irregularly curved shape of the gingiva G within the mouth.

Hereinafter, an operation of the microneedle 1 for dental material delivery according to example embodiments will be described.

Initially, the needle body portion 10 and the base portion 30 of the microneedle 1 may be manufactured using a molding method. Here, the needle body portion 10 may be manufactured by mixing a viscous material, for example, carboxymethyl cellulose, having the mechanical strength sufficient to be adsorbed and thereby inserted into the gingiva G and an active ingredient, for example, lidocaine, by injecting the mixture into the mold M in a state in which the mixture is melted, and by performing natural drying in a state in which bubbles are removed through vacuum processing.

To form the base portion 30, pressure may be applied using a sheet pressing machine by disposing the pellet P on the mold M on which the needle body portion 10 is formed and by removing bubbles through melting processing and vacuum processing.

The base portion 30 and the needle body portion 10 are coupled on the mold M and then separate from the mold M. The active ingredient coating portion 20 may be used to dip-coat the needle body portion 10. The microneedle 1 may be manufactured by performing drying in a room temperature.

In particular, the base portion 30 of the microneedle 1 may be formed using a flexible material, for example, polyethylene, to be effectively adsorbed along the irregularly curved surface of the gingiva G.

Accordingly, since the needle body portion 10 of the microneedle 1 may be easily adsorbed to anywhere of the gingiva G, the active ingredient, for example, dental medicine, included in the needle body portion 10 and the active ingredient coating portion 20 may be effectively delivered to the inside of the gingiva, that is, the gums.

Although a few example embodiments have been shown and described, the present disclosure is not limited to the described embodiments. Instead, it would be appreciated by those skilled in the art that changes may be made to these embodiments without departing from the principles and spirit of the disclosure, the scope of which is defined by the claims and their equivalents.

What is claimed is:

1. A microneedle for dental material delivery, the microneedle comprising:
    a base portion;
    a needle body portion configured to couple with the base portion and including a first viscous material, a second viscous material and a first active ingredient to be transferred to a skin tissue within a mouth, wherein a solubility of the second viscous material against moisture is greater than a solubility of the first viscous material against the moisture;
    an active ingredient coating portion configured to coat a surface of the needle body portion, and including a third viscous material, a fourth viscous material and a second active ingredient to be transferred to the skin tissue within the mouth, wherein a solubility of the fourth viscous material against the moisture is greater than a solubility of the third viscous material against the moisture; and
    wherein the base portion is configured to bend along a skin shape within the mouth,
    wherein the base portion includes at least one polymer selected from the group consisting of polyethylene (PE), polypropylene (PP), polytetrafluoroethylene (PTFE), polymethylmethacrylate (PMMA), ethylene vinyl acetate (EVA), polyurethane (PU), polyethylene terephthalate (PET), polyethylene glycol (PEG), polyvinyl alcohol (PVA), poly lactide (PLA), poly lactic-co-glycolic acid (PLGA), and polyglycolide (PGA), and the base portion further includes polycaprolactone (PCL),
    wherein the at least one polymer selected from the group and the polycaprolactone (PCL) in the base portion are at a weight (%) ratio of 1:9 to 5:5,
    wherein a weight (%) ratio of the first viscous material and the second viscous material in the needle body portion:the first active ingredient in the needle body portion is within a range of 2:1 to 3:1,
    wherein a weight (%) ratio of the fourth viscous material over the third viscous material in the active ingredient coating portion is greater than a weight (%) ratio of the second viscous material over the first viscous material in the needle body portion, and wherein a solubility of the third viscous material and the fourth viscous material included in the active ingredient coating portion against the moisture is greater than a solubility of the first viscous material and the second viscous material included in the needle body portion against the moisture.

2. The microneedle of claim 1, wherein the at least one polymer selected from the group and the polycaprolactone (PCL) in the base portion are at a weight (%) ratio of 1:9 or 2:8.

3. The microneedle of claim 1, wherein the poly lactic-co-glycolic acid (PLGA) and the polycaprolactone (PCL) in the base portion are at a weight (%) ratio of 1:9 to 5:5.

4. The microneedle of claim 1, wherein the needle body portion includes the active ingredient transferred to the skin tissue within the mouth.

5. The microneedle of claim 1, wherein the first viscous material and the second viscous material included in the needle body portion are selected from the group consisting of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, turanose or lactulose and copolymer of monomers constituting the polymer, and cellulose.

6. The microneedle of claim 5, wherein the third viscous material and the fourth viscous material included in the active ingredient coating portion are selected from the group consisting of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, turanose or lactulose and copolymer of monomers constituting the polymer, and cellulose.

7. The microneedle of claim 6, wherein each of the first viscous material included in the needle body portion and the third viscous material included in the active ingredient coating portion is one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, polyvinylpyrrolidone (PVP), hydroxypropyl methyl cellulose (HPMC), ethylcellulose (EC), hydroxypropyl cellulose (HPC), carboxymethyl cellulose, and cyclodextrin, and each of the second viscous material included in the needle body portion and the fourth viscous material included in the active ingredient coating portion is one of maltose, lactose, trehalose, cellobiose, isomaltose, turanose, and lactulose.

8. The microneedle of claim 7, wherein a weight (%) ratio of the first viscous material:the second viscous material:the first active ingredient in the needle body portion is 1 to 7%:1 to 10%:1 to 10%.

9. The microneedle of claim 8, wherein a weight (%) ratio of the first viscous material:the second viscous material:the first active ingredient in the needle body portion is 5%:5%:5%.

10. The microneedle of claim 7, wherein a weight (%) ratio of the third viscous material:the fourth viscous material:the second active ingredient in the active ingredient coating portion is 1 to 10%:1 to 30%:1 to 30%.

11. The microneedle of claim 10, wherein a weight (%) ratio of the third viscous material:the fourth viscous material:the second active ingredient in the active ingredient coating portion is 3%:30%:30%.

12. The microneedle of claim 10, wherein a weight (%) ratio of the third viscous material and the fourth viscous material:the second active ingredient in the active ingredient coating portion is within the range of 1:1 to 1:2.

13. The microneedle of claim 8, wherein the first viscous material is carboxymethyl cellulose (CMC), the second viscous material is maltose, and the first active ingredient is lidocaine.

14. The microneedle of claim 4, wherein each of the first active ingredient included in the needle body portion and the second active ingredient in the active ingredient coating portion includes at least one of lidocaine, mepivacaine, prilocaine, bupivacaine, etidocaine, articaine, procaine, propoxycaine, tetracaine, ropivacaine, butacaine, piperocaine, cocaine, benzocaine, chloroprocaine, proparacaine, and dyclonine.

15. A microneedle for dental material delivery, the microneedle comprising:
   a base portion;
   a needle body portion formed using a water-soluble material and configured to couple with the base portion and including a first viscous material, a second viscous material, and a first active ingredient to be transferred to a skin tissue within a mouth, wherein a solubility of the second viscous material against moisture is greater than a solubility of the first viscous material against the moisture;
   an active ingredient coating portion configured to coat a surface of the needle body portion, and including a third viscous material, a fourth viscous material and a second active ingredient transferred to the skin tissue within the mouth, wherein a solubility of the fourth viscous material against the moisture is greater than a solubility of the third viscous material against the moisture; and
   wherein the base portion is configured to bend along a shape of the gums,
   wherein the base portion is formed by mixing poly lactic-co-glycolic acid (PLGA) and polycaprolactone (PCL) at a weight (%) ratio of 1:9 to 5:5,
   wherein a weight (%) ratio of the first viscous material and the second viscous material:the first active ingredient in the needle body portion is within a range of 2:1 to 3:1, wherein a weight (%) ratio of the fourth viscous material in the active ingredient coating portion is greater than a weight (%) ratio of the second viscous material in the needle body portion, and wherein a solubility of the third viscous material and the fourth viscous material included in the active ingredient coating portion against the moisture is greater than a solubility of the first viscous material and the second viscous material included in the needle body portion against the moisture.

* * * * *